United States Patent
Johnson et al.

(10) Patent No.: US 9,622,818 B2
(45) Date of Patent: Apr. 18, 2017

(54) LIOB BASED HAIR CUTTING DEVICE

(71) Applicant: KONINKLIJKE PHILIPS N.V., Eindhoven (NL)

(72) Inventors: Mark Thomas Johnson, Eindhoven (NL); Calina Ciuhu, Eindhoven (NL); Rieko Verhagen, Eindhoven (NL); Bastiaan Wilhelmus Maria Moeskops, Eindhoven (NL); Kiran Kumar Thumma, Eindhoven (NL); Thomas Adriaan Cohen Stuart, Eindhoven (NL); Petrus Cornelis Paulus Bouten, Eindhoven (NL); Roelof Koole, Eindhoven (NL); Emile Johannes Karel Verstegen, Eindhoven (NL); Petrus Theodorus Jutte, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/405,243

(22) PCT Filed: May 22, 2013

(86) PCT No.: PCT/IB2013/054238
§ 371 (c)(1),
(2) Date: Dec. 3, 2014

(87) PCT Pub. No.: WO2013/182940
PCT Pub. Date: Dec. 12, 2013

(65) Prior Publication Data
US 2015/0202006 A1 Jul. 23, 2015

Related U.S. Application Data

(60) Provisional application No. 61/655,025, filed on Jun. 4, 2012.

(51) Int. Cl.
*A61B 18/20* (2006.01)
*A61B 18/00* (2006.01)

(52) U.S. Cl.
CPC .. *A61B 18/203* (2013.01); *A61B 2018/00476* (2013.01); *A61B 2018/00601* (2013.01); *A61B 2018/202* (2013.01); *A61B 2018/2035* (2013.01)

(58) Field of Classification Search
CPC .................................................. A61B 18/203
See application file for complete search history.

(56) References Cited

U.S. PATENT DOCUMENTS

| | | | | |
|---|---|---|---|---|
| 5,182,857 A | * | 2/1993 | Simon | A61B 18/203 132/118 |
| 6,306,130 B1 | * | 10/2001 | Anderson | A61B 18/203 606/10 |

(Continued)

FOREIGN PATENT DOCUMENTS

| | | |
|---|---|---|
| WO | 9216338 A1 | 10/1992 |
| WO | 2005011510 A1 | 2/2005 |

(Continued)

OTHER PUBLICATIONS

"Plasma Formation in Water by Picosecond and Nanosecond" Nd:YAG Laser Pulses—Part II: Transmission, Scattering, and Reflection Kester Nahen and Alfred Vogel. IEEE Journal of Selected Topics in Quantum Electronics, vol. 2, No. 4, Dec. 1996 861.

(Continued)

*Primary Examiner* — William Thomson
*Assistant Examiner* — John R Downey

(57) ABSTRACT

A laser-based hair cutting device (10) comprises a laser source (18), an optically transparent exit window (15) and optical elements (11, 12, 13, 14). The laser source (18)

(Continued)

provides an incident light beam (21) for cutting a hair (22) above and near a skin surface by laser-induced optical breakdown (LIOB) of the hair (22) in a focal position of the light beam (21). The optically transparent exit window has an external exit surface (15) for allowing the incident light beam (21) to leave the device. The optical elements (11, 12, 13, 14) focus the incident light beam (21) in the focal position at a working distance from the exit surface (15). The working distance is at least $$\frac{1}{\pi NA^2} \sqrt{\frac{2E_p NA^2 \pi}{F_{thresh}} - M^2 \lambda^2}$$

wherein NA is a numerical aperture of the incident light beam leaving the device (10), $E_p$ is a pulse energy (J) of the incident light beam (21), $F_{thresh}$ is a fluence threshold (J/m$^2$) of the exit surface, $M^2$ is a beam quality of the incident light beam (21) and $\lambda$ is a wavelength (m) of the incident light beam (21).

10 Claims, 8 Drawing Sheets

(56) References Cited

U.S. PATENT DOCUMENTS

| | | | | |
|---|---|---|---|---|
| 6,530,919 B1* | 3/2003 | Chodorow | A61B 18/203 606/10 |
| 2002/0173781 A1* | 11/2002 | Cense | A61B 18/203 606/9 |
| 2002/0173782 A1* | 11/2002 | Cense | A61B 18/203 606/9 |
| 2003/0023235 A1* | 1/2003 | Cense | A61B 18/20 606/9 |
| 2006/0178659 A1* | 8/2006 | Van Hal | A61B 18/203 606/2 |
| 2008/0195182 A1* | 8/2008 | Fertner | A61B 18/203 607/88 |
| 2008/0228178 A1* | 9/2008 | Van Hal | A61B 18/203 606/9 |
| 2008/0255548 A1* | 10/2008 | Van Hal | A61B 18/203 606/10 |
| 2008/0319429 A1* | 12/2008 | Van Hal | A61B 18/203 606/9 |
| 2009/0198223 A1* | 8/2009 | Thilwind | A61B 18/24 606/15 |
| 2010/0063490 A1* | 3/2010 | Verhagen | A61B 5/1077 606/9 |
| 2010/0069897 A1* | 3/2010 | Spikker | H01S 3/101 606/9 |
| 2011/0022039 A1* | 1/2011 | Spikker | A61B 18/203 606/9 |
| 2012/0002204 A1* | 1/2012 | Varghese | G01N 21/23 356/369 |
| 2012/0123444 A1* | 5/2012 | Verhagen | A61B 18/20 606/133 |

FOREIGN PATENT DOCUMENTS

| | | |
|---|---|---|
| WO | 2007039854 A1 | 4/2007 |
| WO | 2010032235 A1 | 3/2010 |
| WO | 2011010246 A1 | 1/2011 |
| WO | 2011010546 A1 | 1/2011 |

OTHER PUBLICATIONS

"IR Laser Plasma Interaction With Glass"; Qindeel et al. American Journal of Applied Sciences 4 (12): 1009-1015, 2007.
"Femotosecond Laser Abblation of Transparent Dielectrics; Measurement and Modelisation of Crater Profiles". Guizard S. et al. Applied Surface Science, 186, 364-368, 2002.
"Laser-Induced Surface Damage of Optical Materials; Absorption Sources, Initiation, Growth and Mitigation". S. Papernov et al. Proc. of SPIE vol. 7132, 2008.

* cited by examiner

LIOB BASED HAIR CUTTING DEVICE

This application is the U.S. National Phase application under 35 U.S.C. §371 of International Application No. PCT/IB2013/054238, filed on May 22, 2013, which claims the benefit of U.S. Provisional Application No. 61/655,025 filed on Jun. 4, 2012. These applications are hereby incorporated by reference herein.

FIELD OF THE INVENTION

This invention relates to a laser-based hair cutting device comprising a laser source for providing an incident light beam for cutting a hair above and near a skin surface by laser-induced optical breakdown (LIOB) of the hair in a focal position of the light beam, optical elements for focusing the incident light beam in the focal position, at a working distance from an exit surface for allowing the incident light beam to leave the device.

BACKGROUND OF THE INVENTION

Such laser-based hair cutting devices are, e.g., disclosed in the international patent application published as WO 2011/010246. Said international patent application describes such a device for shortening hairs comprising a laser source for generating a laser beam during a predetermined pulse time, an optical system for focusing the laser beam into a focus spot and a laser beam manipulator for positioning the focal spot in the target position. A dimension of the focal spot and a power of the generated laser beam are such that in the focal spot the laser beam has a power density which is above a characteristic threshold value for hair tissue, above which, for the predetermined pulse time, a laser-induced optical breakdown (LIOB) phenomenon occurs in the hair tissue. An optical blade with a tapered end guides the laser beam in a direction substantially parallel to the skin surface towards the hairs that are cut at a height just above the skin.

In general, laser-induced optical breakdown (LIOB) occurs in media, which are transparent or semi-transparent for the wavelength of a pulsed laser beam, when the power density of the laser beam in the focal spot exceeds a threshold value which is characteristic for the particular medium. Below the threshold value, the particular medium has relatively low linear absorption properties for the particular wavelength of the laser beam.

Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

From experiments it appeared that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density (W/cm$^2$) decreases when the pulse time increases. It appeared that in order to achieve mechanical effects as a result of the LIOB phenomenon which are sufficiently effective to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ W/cm$^2$. For the described pulse time and with a sufficiently small focal spot size obtained, for example, by means of a lens having a sufficiently large numerical aperture, this threshold value can be achieved with a total pulse energy of only a few tenths of a mJ.

Whilst it is possible, using the device of WO 2011/010546, to generate a laser-induced optical breakdown (LIOB) from an incident beam leaving the device through the exit surface of an optical blade and having sufficient energy to cut human hairs, the products of the LIOB (shock wave, plasma, high irradiance) can cause destructive damage to the exit surface. A damaged blade has a detrimental effect on the ability of the device to provide a tight focus at the desired position, which may reduce the efficacy of the shaving process and/or may increase the occurrence of adverse side effects, such as skin irritation.

OBJECT OF THE INVENTION

It is an object of the invention to provide a skin treatment system wherein LIOB-caused damage to the exit surface is reduced.

SUMMARY OF THE INVENTION

According to a first aspect of the invention, this object is achieved by providing a laser-based hair cutting device comprising a laser source for providing an incident light beam for cutting a hair above and near a skin surface by laser-induced optical breakdown (LIOB) of the hair in a focal position of the light beam, an optically transparent exit window with an external exit surface for allowing the incident light beam to leave the device, optical elements for focusing the incident light beam in the focal position at a working distance from the exit surface, wherein the laser source and the optical elements are arranged and configured such that the working distance is at least $$\frac{1}{\pi NA^2}\sqrt{\frac{2E_p NA^2 \pi}{F_{thresh}} - M^2 \lambda^2}$$

wherein NA is a numerical aperture of the incident light beam leaving the device, $E_p$ is a pulse energy (J) of the incident light beam, $F_{thresh}$ is a fluence threshold (J/m$^2$) of the exit surface, $M^2$ is a beam quality of the incident light beam and $\lambda$ is a wavelength (m) of the incident light beam.

Experiments have shown that damage of the exit surface originating from the light intensity of the laser beam and LIOB-induced shockwaves can, to a large extent, be avoided by a judicious choice of exit surface material. Surprisingly, exit surface material capable of sufficiently reducing damage originating from plasma impact is not readily available. From many LIOB experiments, using different exit surface materials, laser beam properties and optical elements, the inventors have deduced the above mentioned relation between the most important system parameters and the minimum working distance required for restricting plasma damage. An important consequence of the results obtained is that the desired working distance turns out to be much larger than that previously applied. While it was common to cut hairs much closer to the blade surface, the newly found relation implies that working distances of at least 150 µm, but preferably 200 or even 300 µm should be used, depending on the relevant beam parameters.

In the above shown relation between the minimum working distance and other operational parameters, the fluence threshold is a measure for the total amount of energy that has to be provided to a unit surface area (e.g. 1 cm$^2$) by one pulse of the incident light beam, before damage occurs. This threshold is more or less independent of the exact material of the exit surface. The fluence threshold depends on the pulse duration (shorter pulses, higher fluence threshold) and laser wavelength (shorter wavelength, higher fluence threshold). Standard formulas for determining the fluence threshold are known from the literature.

The beam quality of a laser beam can be defined in different ways, but is essentially a measure of how tightly a laser beam can be focused under certain conditions (e.g. with a limited beam divergence). The most common ways to quantify the beam quality are the beam parameter product (BPP) or the M$^2$ factor. The BPP is defined as the product of the beam radius at the beam waist and the far-field beam divergence angle. The M$^2$ factor is defined as the beam parameter product divided by the corresponding product for a diffraction-limited Gaussian beam with the same wavelength. For an ideal beam, M$^2$ approaches 1. In most examples described in this application M$^2$ is about 1.2. However, also beams with an M$^2$ factor up to 10 or even higher can be used for LIOB-based hair cutting.

In an embodiment of the hair cutting device according to the invention, a mechanical spacer is provided for positioning the hair at the focal position. When a distance between a front surface of the spacer and the exit surface is equal to or approximately equal to the working distance, a hair resting against the spacer's front surface will be cut due to LIOB in the focal position of the laser beam.

The spacer may be an integral part of an optical blade comprising the exit surface and being arranged to guide the light beam in a direction substantially parallel to the skin surface. Alternatively, the mechanical spacer is an integral part of a stretcher element which is used, during use of the hair cutting device, for stretching the skin surface and lifting the hair in front of an optical blade relative to a shaving direction. When the device is pulled over the skin surface, the stretcher element stretches and smoothens the skin, thereby lifting the hairs just behind the stretcher element. The spacer element then holds the hair in an upright position at the right distance to the exit surface of the optical blade, such that the hair can be cut by the laser beam. Of course, also when the spacer is an integral part of the optical blade or a completely separate feature, a mechanical stretcher may be provided for stretching the skin surface and lifting the hair.

Optionally, the exit surface is an external surface of a transparent protective layer placed on the exit window, the protective layer having a higher resistance to LIOB damage than the exit window itself. Transparent here means largely transparent at least to light of the wavelength of the laser beam. The damage-resistant layer is provided for providing protection in the event of any LIOB events that may still occur at too close a distance from the exit surface. An advantage of using a protective layer is that other transparent elements, such as an optical blade, can be made of cheaper and/or easier moldable material like glass or plastics, while a more durable material is used for the exit surface that needs to be protected against LIOB-induced damage. Suitable examples of materials for the transparent protective layer are sapphire, alumina, diamond, spinel, YAG, GaN or carbides. When no protective layer is used, the exit window itself is preferably made of such damage resistant materials.

The protective layer is preferably releasably secured to the exit window. When the protective layer is damaged, it can be replaced by a new undamaged one and the damage will not have a detrimental effect on the operation of the hair cutting device. The protective layer may be made of a flexible and transparent polymer. Polymers are cheap and easily moldable. The device may further comprise a mold for molding the polymer into a desired, undamaged shape and positioning the shaped polymer at the exit surface where it functions as the protective layer. After being used as a protective layer, the polymer may, e.g., be removed by the device and collected in a waste basket or may be redirected to the mold for recycling.

These and other aspects of the invention are apparent from and will be elucidated with reference to the embodiments described hereinafter.

DETAILED DESCRIPTION OF THE INVENTION

Figure 1:
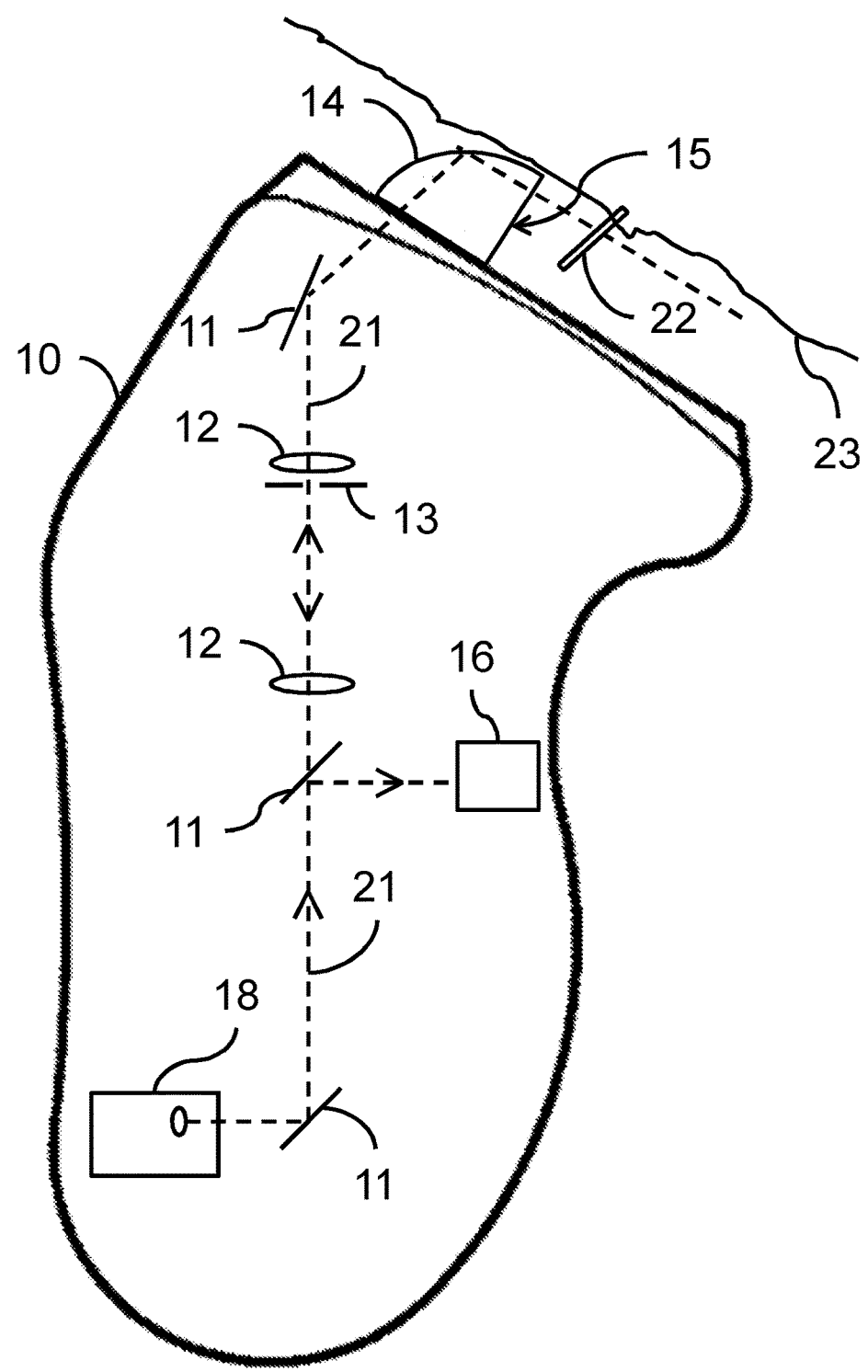
FIG. 1 schematically shows a laser shaver according to the invention.

FIG. 1 schematically shows a laser shaver 10 according to the invention. The laser shaver 10 is provided for optically cutting hairs 22 by focusing a laser beam 21 with sufficiently high power inside the hairs 22. The laser beam 21 is provided by a laser source 18, which may comprise a laser diode. For example, pulsed Nd:YAG lasers with emission at 1064 nm or Er:YAG lasers with emission at 1645 nm are used for LIOB cutting of the hairs 22. The light beam 21 leaves the laser shaver 10 via the transparent exit window. In this laser shaver 10 the exit window is embodied as an optical blade 14 which also directs the light beam 21 in a direction, more or less parallel to the skin 23 (when the device 10 is in operation). The light 21 leaves the device 10 at an exit surface 15 of the optical blade 14. Optical elements, such as lenses 12, mirrors 11, a pinhole 13 and the optical blade 14 are provided for focusing the pulsed laser beam 21 in the hair 22. The optical elements 11, 12, 13, 14 may be adjustable by a focusing device (not shown) for adapting the exact position of the focal point when needed. The focusing device may adjust the exact trajectory of the light beam 21 and the position of the focus by rotating and/or displacing the optical elements 11, 12, 13, 14.

Part of the light 21 reaching the skin 23 or hair 22 is reflected or scattered at the skin 23 or hair 22 tissue and re-enters the device 10 via the exit surface 15. The laser shaver 10 of FIG. 1 may additionally comprise a detection unit 16 for detecting the light beam 21 after it has been reflected, scattered or otherwise interacted with at the skin 23 or hair 22 tissue. The detection unit 16 may comprise one or more photodiodes and may be arranged to detect only light having a predefined polarization direction. It may also comprise multiple channels for separately measuring different polarization components. Such detection units 16 are usually provided in laser shavers 10 for performing hair detection. The light source 18 and the focusing device are preferably operated in dependence on the detection signals from the detection unit 16 in order to aim the laser beam 21 at detected hairs only and to reduce skin 23 irritation or damage to the exit surface 15 due to unnecessary laser pulses and LIOB events.

According to the invention, the working distance of the device 10 is at least $$\frac{1}{\pi NA^2}\sqrt{\frac{2E_p NA^2 \pi}{F_{thresh}} - M^2\lambda^2}$$

wherein NA is the numerical aperture of the incident light beam 21 leaving the device 10, $E_p$ is a pulse energy of the incident light beam 21, $F_{thresh}$ is a fluence threshold of the exit surface 15, $M^2$ is a beam quality of the incident light beam 21 and $\lambda$ is a wavelength of the incident light beam 21.

The fluence threshold is more or less independent of the exact material of the exit surface 15 and is a measure of the total amount of energy to be provided to a unit surface area (e.g. 1 cm$^2$) by one pulse of the incident light beam 21 before damage occurs. The fluence threshold depends on the pulse duration (shorter pulses, higher fluence threshold) and laser wavelength (shorter wavelength, higher fluence threshold). Standard formulas for determining the fluence threshold are known from the literature. For three different wavelengths and five different pulse durations, exemplary fluence thresholds (J/cm$^2$) are provided in the table below.

|         | 6 ns  | 10 ns | 20 ns | 50 ns | 100 ns |
|---------|-------|-------|-------|-------|--------|
| 800 nm  | 19.2  | 28    | 50    | 115   | 220    |
| 1064 nm | 11.4  | 16    | 28    | 65    | 130    |
| 1645 nm | 5.28  | 7.4   | 12.6  | 28    | 54     |

Beam quality ($M^2$) of a laser beam is a dimensionless parameter describing how well the laser beam can be focused. For an ideal beam, $M^2$ approaches 1. In most examples described in this application $M^2$ is about 1.2. However, also beams with an $M^2$ factor up to 10 or even higher can be used for LIOB-based hair cutting.

When using typical values ($\lambda$=800 nm, $E_p$=10 mJ, a NA=0.5, good beam quality ($M^2$ about 1.2) and a 50 ns pulse duration) for the various parameters in the equation above, a minimum working distance of at least 150 microns is needed to substantially reduce the amount of LIOB-induced damage to the exit surface 15. For a further reduction of damage to the exit surface or when different parameter values are used, working distances of more than 200 or even 300 microns may be needed.

For typical incident light beams with a pulse energy of 10 mJ, NA=0.8 and good beam quality ($M^2$ about 1.2), the following table approximately shows the minimal working distances (microns) for different wavelengths (nm) and pulse durations (ns):

|         | 6 ns | 10 ns | 20 ns | 50 ns | 100 ns |
|---------|------|-------|-------|-------|--------|
| 800 nm  | 228  | 188   | 141   | 93    | 67     |
| 1064 nm | 295  | 249   | 188   | 124   | 87     |
| 1645 nm | 434  | 367   | 281   | 188   | 136    |

With a similar incident light beam, but NA=0.5, the approximate minimal working distance is:

|         | 6 ns | 10 ns | 20 ns | 50 ns | 100 ns |
|---------|------|-------|-------|-------|--------|
| 800 nm  | 364  | 302   | 226   | 149   | 108    |
| 1064 nm | 473  | 399   | 302   | 198   | 140    |
| 1645 nm | 695  | 587   | 450   | 302   | 217    |

Figure 2:
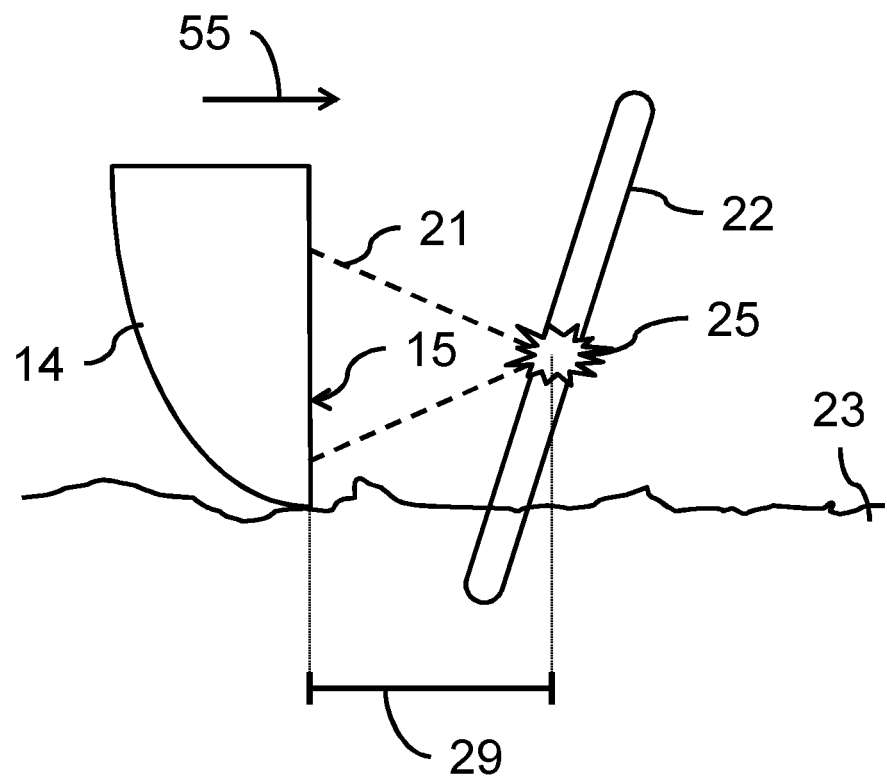
FIG. 2 shows a close up of an optical blade passing over a skin surface.

FIG. 2 shows a close-up of an optical blade 14 passing over a skin surface 23. The light beam 21 leaves the device 10 at the exit surface 15 of the optical blade 14. The light beam leaves the device 10 in a direction substantially parallel to the skin surface 23, such that the focus of the light beam 21 is located inside the hair 22. 'Substantially parallel', is to be understood to include also small angles with respect to the skin surface 23 which still allow the light beam 21 to have its focal point inside a hair 22 and above the skin surface 23 (see, e.g., FIG. 5).

The power density of the laser beam 21 in the focal spot is such that it exceeds the LIOB threshold value for hair tissue. Consequently, a LIOB event 25 occurs inside the hair tissue, thereby cutting the hair 22. During use, the optical blade 14 of the device 10 is moved along the skin surface 23 in a shaving direction 55 such that multiple hairs 22 are cut off successively. The working distance 29 of the device, i.e. the distance between the exit surface 15 and the focal point where the LIOB event 25 takes place, satisfies the equation shown above in order to minimize or completely avoid LIOB induced damage to the exit surface 15.

Figure 3:
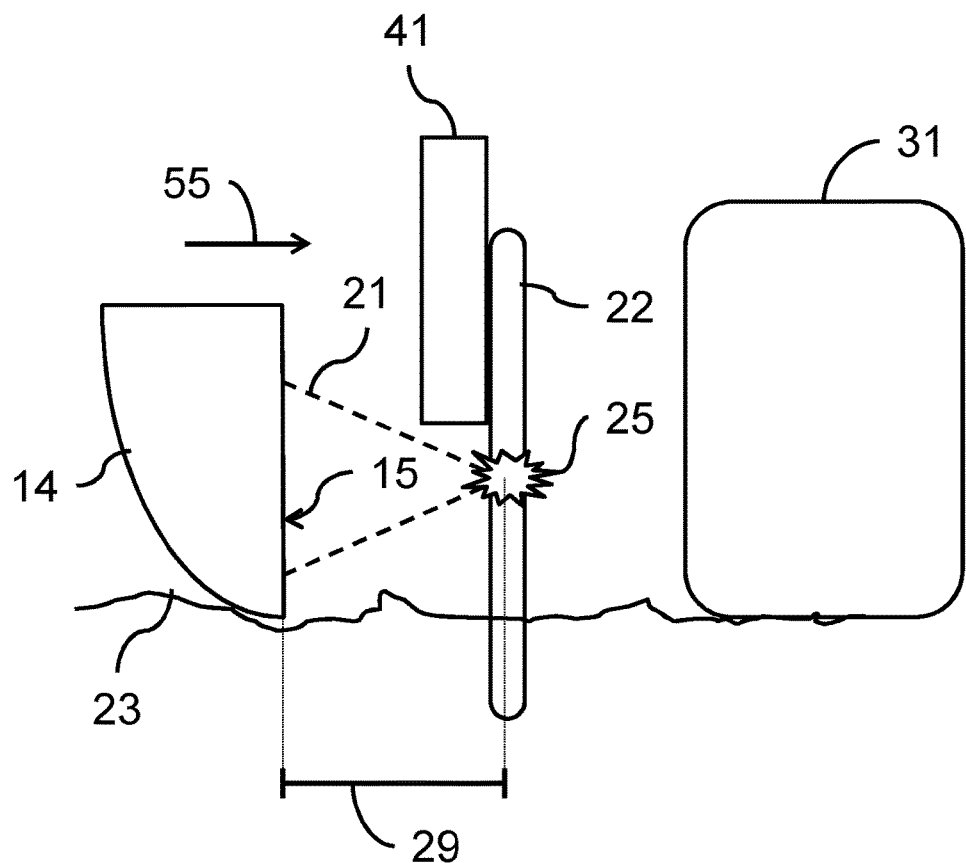
FIG. 3 shows an optical blade, a stretcher element and a spacer passing over a skin surface.

The close-up in FIG. 3 shows an embodiment that further comprises a stretcher element 31 and a spacer 41. When the device 10 is pulled over the skin surface 23, the stretcher element 31 stretches and smoothens the skin 23, thereby lifting the hairs 22 just behind the stretcher element 31. The spacer element 41 then holds the hair 22 in a more upright position at the right distance to the exit surface 15 of the optical blade 14, such that the hair 22 can be cut by the laser beam 21. The 'right' distance herein corresponds to the working distance 29 of the device 10 which at least satisfies the equation disclosed above. In addition to manipulating the hair 22 in such a way that the focal point of the light beam 21 coincides with the hair 22, the spacer element 41 may provide some shielding against the damaging effects of the LIOB event 25. Both the stretcher element 31 and the spacer element 41 are typically made of plastics, but metals or other materials or combinations of materials may also be used. The spacer element 41 may be attached to, or may be an integral part of, the stretcher element 31, the optical blade 14 or the device housing. Different shapes may be useful as long as they effectively keep the hairs 22 at or close to the working distance 29 of the device 10.

Figure 4:
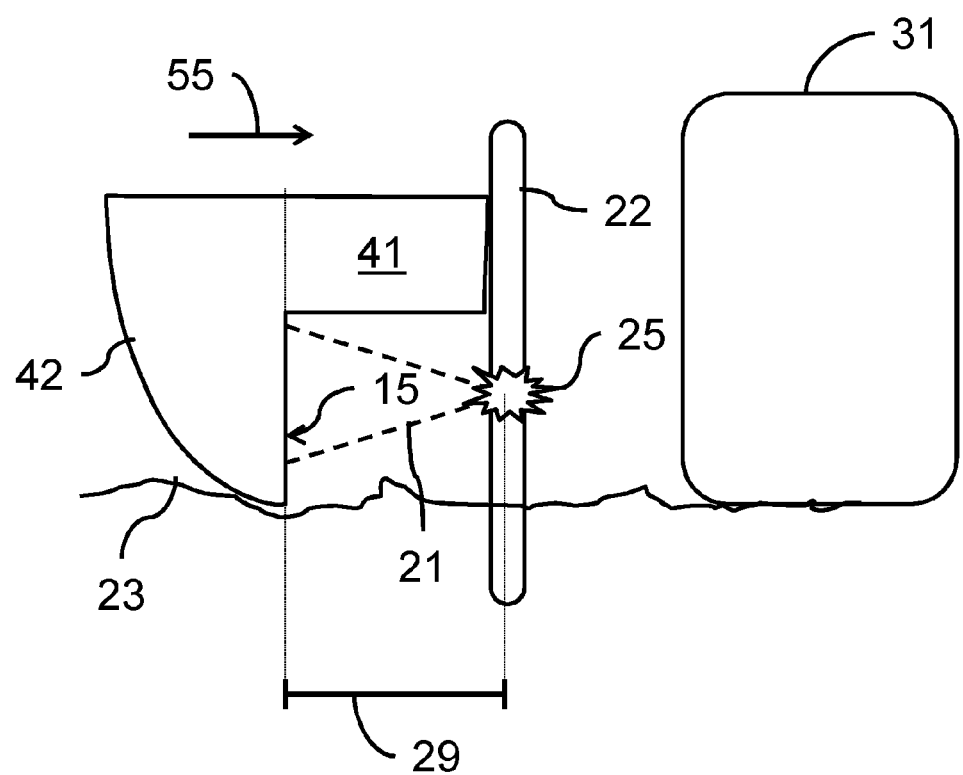
FIG. 4 shows an optical blade with an integrated spacer.

FIG. 4 shows an optical blade 42 with an integrated spacer 41. The spacer part 41 of the optical blade 42 may or may not be made of the same material as the rest of the optical blade 42. The spacer part 41 does not have to be transparent or LIOB-resistant.

Figure 5:
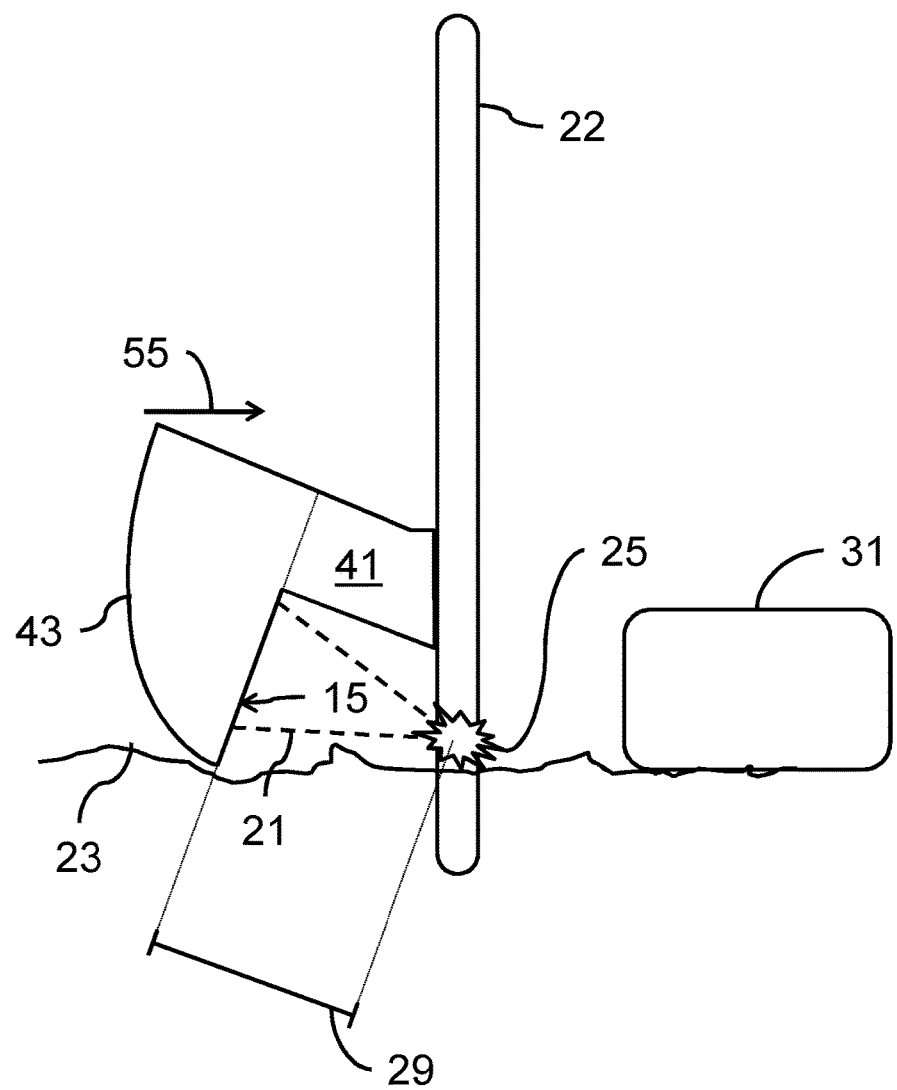
FIG. 5 shows a different optical blade with an integrated spacer.

FIG. 5 shows a different optical blade 43 with an integrated spacer 41. In this embodiment, the light beam 21 makes a small angle with the skin surface 23. This has the advantage that the hair 22 is cut at a position closer to the skin surface 23. The function of the spacer part 41 of the optical blade 43 is the same as that of the spacer element and spacer part 41 in the previous figures. Again, other shapes may be equally useful. It is important only that the spacer part 41 effectively keeps the hairs 22 at or close to the working distance 29 of the device 10.

Figure 6:
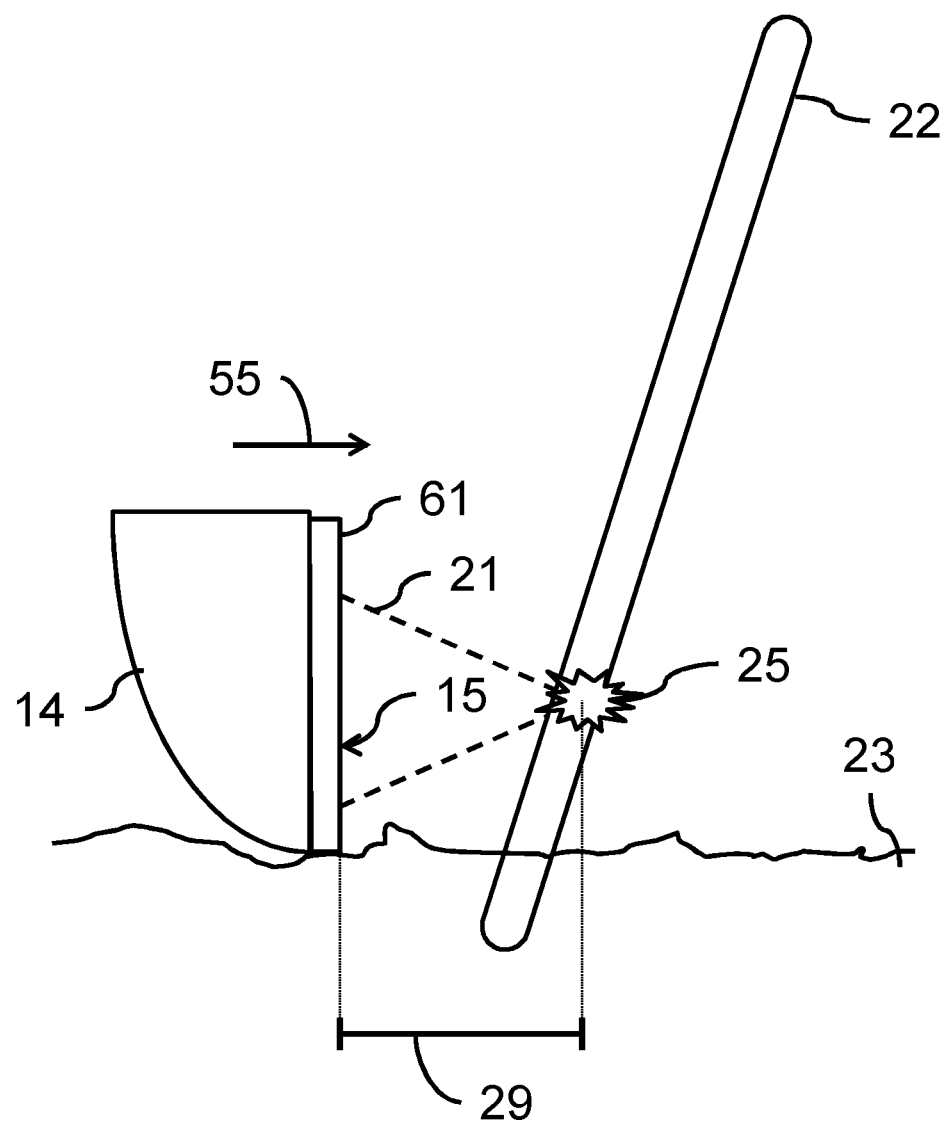
FIG. 6 shows an optical blade with a protective layer.

FIG. 6 shows an exit window, here in the form of an optical blade 14, with a protective layer 61. The protective layer 61 is made of a material with a high LIOB damage resistance, at least higher than the LIOB damage resistance of the exit window itself, and is transparent to light of the wavelength of the light beam 21. The protective layer 61 comprises the exit surface 15 through which the light beam 21 leaves the device 10. The protective layer 61 is provided for providing protection in the event of any LIOB events 25 that may still occur at too close a distance from the exit surface, e.g. because of focusing problems or unexpected reflections. An advantage of the use of the protective layer 61 is that other transparent elements, such as an optical blade 14, can be made of cheaper and/or easier moldable material like glass or plastics, while a more durable material is used for the exit surface 15 that needs protection against LIOB-induced damage.

Suitable examples of materials for the transparent protective layer 61 are sapphire, alumina, diamond, spinel, YAG, GaN or carbides. The protective layer 61 is preferably releasably secured to the optical blade 14. When the protective layer 61 is damaged, it can be replaced by a new undamaged one and the damage will not have a detrimental effect on the operation of the hair cutting device 10. Replacement or repair of the protective layer may, e.g., be performed when the shaver device 10 is placed in a docking station.

The protective layer 61 may be made of a flexible and transparent polymer. Polymers are cheap and easily moldable. It is important that the polymer 61 exhibits minimal absorption of the laser light, which can be obtained by selecting a polymer 61 that is transparent to the wavelength of the light beam 21 and/or by using a thin layer of polymer 61 to protect the blade 14. For example, fluorinated polymers such as AF1600 do not absorb the 1645 nm laser wavelength of an Er:YAG laser. A further advantage of AF1600 is that its refractive index matches the refractive index of water. When the protective layer 61 has a refractive index similar to that of the immersion fluid (e.g. water), the light beam is minimally affected by any damage in the protective layer 61.

The polymer preferably is flexible enough to withstand the LIOB shockwave. Furthermore, it is desired that the polymer 61 is resistant to the high thermal load of the plasma. Suitable polymer materials might be acrylates, silicones, polycarbonates, parylene or polyimides. An advantage of polycarbonates is that they are very resistant against cracking or breaking. Parylene and polyimides can withstand high temperatures.

Figure 7:
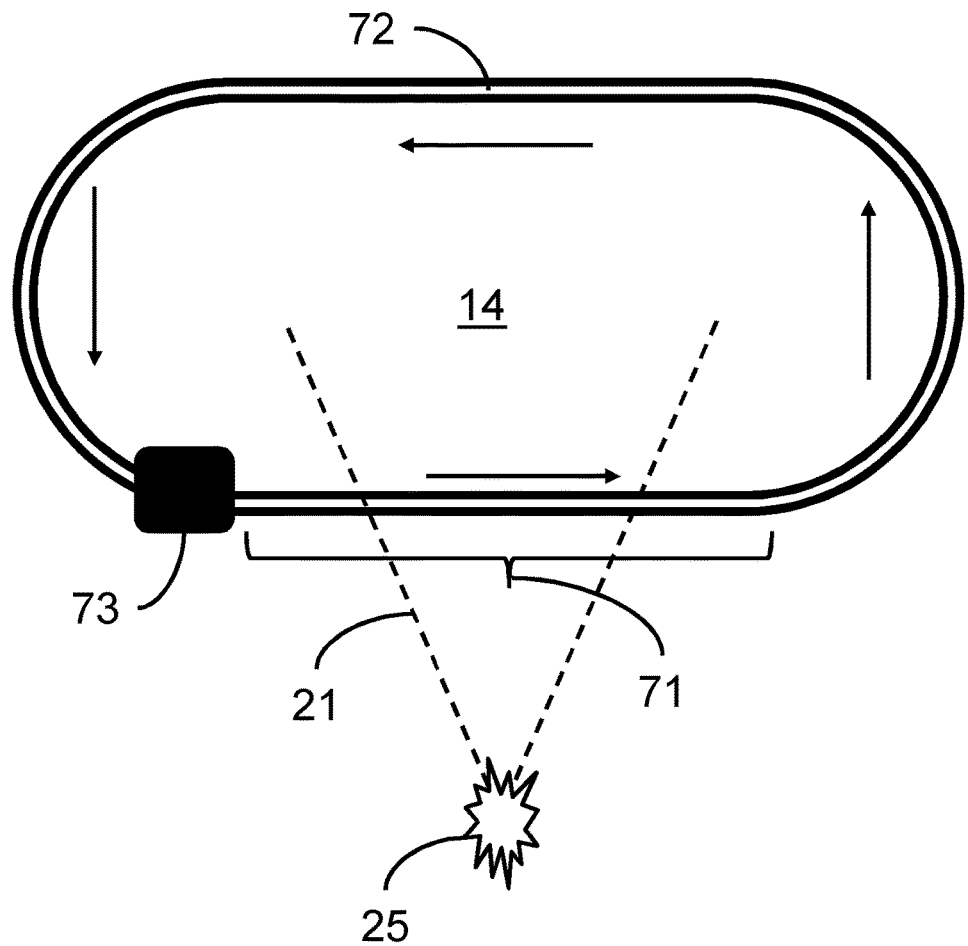
FIG. 7 shows an optical blade with a replaceable and recyclable protective layer.

FIG. 7 shows an optical blade 14 with a moldable and replaceable polymer protective layer 71. The device in FIG. 7 uses a polymer strip 72 which is at least temporarily able to function as a protective layer 71 and to shield the exit surface of the optical blade 14 from LIOB damage. The protective layer 71 is positioned in between the optical blade and the position of the LIOB formation 25. When, e.g., after a fixed number of shaves or laser pulses, damage to the shield 71 is detected or when a user initiates a replacement protocol, the strip 72 is moved such that a fresh and undamaged part of it takes over the function of the protective layer 71. Alternatively, the strip 72 is moved continuously and/or steadily, such that a damaged part cannot be hit by the light beam twice. The device 10 further comprises a mold 73 for molding the polymer 72 into an undamaged shape and positioning the shaped polymer at the exit surface of the optical blade 14 where it functions as the protective layer 17. The use of this mold 73 makes it possible to recycle used parts of the strip 72 and to provide fresh protective layers 71 without having to supply new protective layer material.

Figure 8:
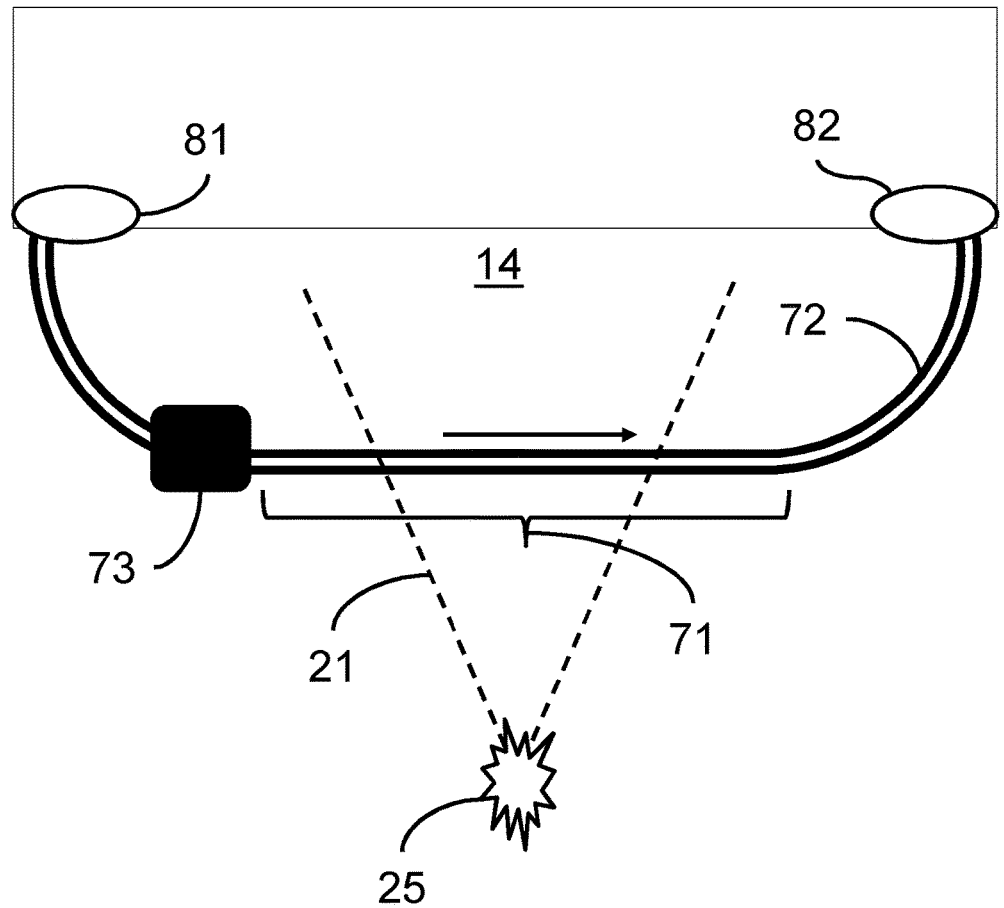
FIG. 8 shows an optical blade with a moldable and replaceable protective layer.

FIG. 8 shows an optical blade 71 construction similar to that of FIG. 7. However, in this embodiment the polymer strip 72 is not recycled. The mold 73 uses polymer from a refillable polymer reservoir 81 for creating a fresh undamaged protective layer 71. After being used as a protective layer 71, the polymer is removed from the exit surface and, e.g., collected in a waste basket 82.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:
1. A laser-based hair cutting device comprising:
a housing;
a laser source disposed within the housing for providing an incident light beam for cutting a hair above and near a skin surface by laser-induced optical breakdown (LIOB) of the hair in a focal position of the light beam;
an optically transparent exit window coupled to the housing with an external exit surface for allowing the incident light beam to leave the housing; and
optical elements disposed within and on the housing for focusing the incident light beam in the focal position at a working distance away from the exit surface, wherein the laser source, the optically transparent exit window, and the optical elements are arranged and configured to provide (i) a numerical aperture NA of the incident light beam leaving the housing, (ii) a pulse energy $E_p$ (J) of the incident light beam, (iii) a fluence threshold $F_{thresh}$ (J/m$^2$) of the exit surface, (iv) a beam quality M$^2$ of the incident light beam, and (v) a wavelength λ (m) of the incident light beam, such that the working distance away from the exit surface, given by the expression

$$\frac{1}{\pi NA^2}\sqrt{\frac{2E_p NA^2\pi}{F_{thresh}} - M^2\lambda^2},$$

comprises at least 150 μm for minimizing or completely avoiding a destructive damage to the exit surface caused by products of LIOB that include LIOB-induced shock waves, plasma, and a light intensity of the incident light beam.

2. The laser-based hair cutting device as claimed in claim 1, further comprising a mechanical spacer coupled to the housing for positioning the hair at least the working distance away from the exit surface of the optically transparent exit window at the focal position.

3. The laser-based hair cutting device as claimed in claim 2, further comprising an optical blade coupled to the housing, wherein the optical blade comprises the exit surface and is arranged to guide the light beam in a direction parallel to the skin surface, further wherein the mechanical spacer comprises an integral part of the optical blade.

4. The laser-based hair cutting device as claimed in claim 2, further comprising:
an optical blade coupled to the housing, wherein the optical blade comprises the exit surface and is arranged to guide the light beam in a direction parallel to the skin surface, and
a stretcher element for stretching, during use of the hair cutting device, the skin surface and lifting the hair in front of the optical blade relative to a shaving direction, wherein the mechanical spacer is an integral part of the stretcher element.

5. The laser-based hair cutting device as claimed in claim 1, wherein the exit surface comprises sapphire, alumina, diamond, spinel, YAG, GaN or carbides.

6. The laser-based hair cutting device as claimed in claim 1, wherein the exit surface comprises an external surface of a transparent protective layer placed on and releasably secured to the exit window, the protective layer having a higher resistance to LIOB damage than the exit window.

7. The laser-based hair cutting device as claimed in claim 6, wherein the protective layer comprises sapphire, alumina, diamond, spinel, YAG, GaN or carbides.

8. The laser-based hair cutting device as claimed in claim 6, wherein the protective layer has a thickness of at least 50 μm.

9. The laser-based hair cutting device as claimed in claim 6, wherein the protective layer comprises a flexible and transparent polymer.

10. The laser-based hair cutting device as claimed in claim 9, wherein the flexible and transparent polymer further comprises a molded polymer having an undamaged shape positioned at the exit surface where it functions as the protective layer.

* * * * *